US010507258B2

United States Patent
Sevy (10) Patent No.: US 10,507,258 B2
(45) Date of Patent: Dec. 17, 2019

(54) COMPACT, MOBILE, MODULAR, INTEGRATED DIFFUSER APPARATUS AND METHOD

(71) Applicant: Earl Vaughn Sevy, Cedar City, UT (US)

(72) Inventor: Earl Vaughn Sevy, Cedar City, UT (US)

( * ) Notice: Subject to any disclaimer, the term of this patent is extended or adjusted under 35 U.S.C. 154(b) by 168 days.

(21) Appl. No.: 15/401,346

(22) Filed: Jan. 9, 2017

(65) Prior Publication Data

US 2017/0112956 A1    Apr. 27, 2017

Related U.S. Application Data

(60) Continuation-in-part of application No. 15/373,035, filed on Dec. 8, 2016, and a continuation-in-part of application No. 15/297,542, filed on Oct. 19, 2016, now Pat. No. 9,943,621, which is a division of application No. 14/260,520, filed on Apr. 24, 2014, now Pat. No. 9,480,769, which is a continuation-in-part of application No. 13/854,545, filed on Apr. 1, 2013, now Pat. No. 9,415,130.

(60) Provisional application No. 62/277,343, filed on Jan. 11, 2016, provisional application No. 62/265,820, filed on Dec. 10, 2015.

(51) Int. Cl.
*A61L 9/14* (2006.01)
*A61L 9/20* (2006.01)

(52) U.S. Cl.
CPC ............... *A61L 9/14* (2013.01); *A61L 9/205* (2013.01); *A61L 2209/11* (2013.01); *A61L 2209/13* (2013.01); *A61L 2209/14* (2013.01)

(58) Field of Classification Search
CPC ........ A61L 9/14; A61L 9/205; A61L 2209/14; A61L 2209/11; A61L 2209/13
USPC .................................. 239/6, 34–60, 343, 370
See application file for complete search history.

(56) References Cited

U.S. PATENT DOCUMENTS 904,149 A    11/1908  Rachmann
2,826,454 A    3/1958  Coanda
(Continued)

FOREIGN PATENT DOCUMENTS

CA          2519809      10/2004
DE     202013105614 U1    2/2014
(Continued)

OTHER PUBLICATIONS

Tetra Whisper Aquarium Air Pump 300, Aquarium Guys, Oct. 8, 2008 p. 1, http://www.aquariumguys.com/tetraairpump4.html.
(Continued)

*Primary Examiner* — Alexander M Valvis
*Assistant Examiner* — Qingzhang Zhou
(74) *Attorney, Agent, or Firm* — Pate Baird, PLLC (57) ABSTRACT

A new diffuser for essential oils and the like is rendered more compact by integrating the entire diffuser into a form of cap threaded to fit a bottle operating as a reservoir. The motor and pump system are integrated into a package sleeved inside a housing that then receives in a silo beside the pump and motor the entire reservoir and diffuser system. Simplified control algorithms provide a limited set of buttons that are more intuitive by which a user need only define total time of operation, some level of intensity of scent, and an indication of the comparative size of the space to be conditioned by the diffused scent.

17 Claims, 9 Drawing Sheets

(56) References Cited

U.S. PATENT DOCUMENTS

| | | | |
|---|---|---|---|
| 3,112,074 A | 11/1963 | Green | |
| 3,515,966 A | 6/1970 | De Valroger et al. | |
| 3,641,757 A | 2/1972 | Rehn | |
| 4,235,611 A | 11/1980 | Brownell | |
| 4,243,396 A | 1/1981 | Cronenberg | |
| D282,283 S | 1/1986 | Weigl et al. | |
| 4,976,259 A | 12/1990 | Higson et al. | |
| 5,029,759 A | 7/1991 | Weber | |
| 5,054,477 A | 10/1991 | Terada et al. | |
| 5,137,432 A | 8/1992 | Tsai | |
| 5,201,641 A | 4/1993 | Richer | |
| 5,248,448 A | 9/1993 | Waldron et al. | |
| 5,309,900 A | 5/1994 | Knoch et al. | |
| 5,314,529 A | 5/1994 | Tilton et al. | |
| D350,190 S | 8/1994 | Clawson et al. | |
| 5,449,117 A * | 9/1995 | Muderlak | A47K 17/00 222/646 |
| 5,549,247 A | 8/1996 | Rossman et al. | |
| 5,579,758 A | 12/1996 | Century | |
| 5,687,710 A | 11/1997 | Ambrosio et al. | |
| 5,875,774 A | 3/1999 | Clementi et al. | |
| 5,922,247 A | 7/1999 | Shoham et al. | |
| 6,029,913 A | 2/2000 | Stroia et al. | |
| D434,843 S | 12/2000 | Zaragoza et al. | |
| 6,168,392 B1 | 1/2001 | Takano | |
| 6,217,281 B1 | 4/2001 | Jeng et al. | |
| 6,236,042 B1 | 5/2001 | Kato et al. | |
| 6,364,637 B1 | 4/2002 | Hase et al. | |
| 6,669,176 B2 | 12/2003 | Rock | |
| 6,672,129 B1 * | 1/2004 | Frederickson | A61M 15/02 347/20 |
| D491,259 S | 6/2004 | Garrison et al. | |
| D491,258 S | 7/2004 | Sevy | |
| D492,020 S | 7/2004 | Sevy | |
| D509,893 S | 9/2005 | Sevy | |
| 6,968,069 B1 | 11/2005 | Zhao | |
| D520,129 S | 5/2006 | Sevy | |
| D526,710 S | 7/2006 | Sevy | |
| 7,407,118 B2 | 8/2008 | Sevy | |
| D582,533 S | 12/2008 | Bodine | |
| 7,476,870 B2 | 1/2009 | Hopaluk et al. | |
| D590,931 S | 4/2009 | Kennedy et al. | |
| 7,712,683 B2 | 5/2010 | Robert et al. | |
| 7,878,418 B2 * | 2/2011 | Sevy | A61M 11/06 128/200.18 |
| 7,930,068 B2 | 4/2011 | Robert et al. | |
| D639,386 S | 6/2011 | Cummings et al. | |
| 8,001,963 B2 | 8/2011 | Giroux | |
| D682,909 S | 5/2013 | Kim | |
| D697,605 S | 1/2014 | Anderson, Jr. et al. | |
| D716,427 S | 10/2014 | Lim et al. | |
| 9,415,130 B2 | 8/2016 | Sevy | |
| 2007/0159422 A1 | 7/2007 | Blandino et al. | |
| 2008/0031784 A1 | 2/2008 | Bistritzky et al. | |
| 2008/0251608 A1 * | 10/2008 | Robert | A61L 9/14 239/346 |
| 2008/0283049 A1 | 11/2008 | Mahoney et al. | |
| 2009/0127357 A1 * | 5/2009 | Suda | A23B 7/158 239/704 |
| 2009/0162253 A1 * | 6/2009 | Porchia | A01M 1/2072 422/124 |
| 2010/0084484 A1 * | 4/2010 | Sevy | A61M 11/06 239/4 |
| 2010/0206306 A1 * | 8/2010 | Feriani | A61M 11/00 128/203.12 |
| 2011/0132992 A1 * | 6/2011 | Hoppe | A61L 9/02 239/6 |
| 2013/0327323 A1 | 12/2013 | Rubin | |
| 2017/0274405 A1 * | 9/2017 | Lucas | B05B 17/0646 |
| 2017/0281821 A1 * | 10/2017 | Davis, II | B05B 17/0607 |

FOREIGN PATENT DOCUMENTS

| | | |
|---|---|---|
| FR | 2873587 A1 | 2/2006 |
| GB | 2485280 | 5/2012 |
| JP | 2001046920 | 9/2002 |

OTHER PUBLICATIONS

Optima Air Pump A807, Aquarium Guys, Oct. 8, 2008, p. 1, http://www.aquariumguys.com/optimaairpump.html.

Silent Air X-4 Air Pump, Aquarium Guys, Oct. 8, 2008, p. 1, http://www.aquariumguys.com/silentairpump4.html.

Whisper 60 Aquarium Air Pump, Aquarium Guys, Oct. 8, 2008, p. 1, http://www.aquariumguys.com/tetra-whisper60-air-pump.html.

Rena Air 400 Air Pump 702E, Aquarium Guys, Oct. 8, 2008, p. 1, http://www.aquariumguys.com/renaairpump4.html.

Tom Stellar Air Pumps S-30, Fish Tanks Direct, Oct. 8, 2008, p. 1, http://www.fishtanksdirect.com/index.asp?PageAction=Viewprod&ProdID=2102.

Aroma-Globe ™ Essential Oil Diffuser/Nebulizer Diffuser World, Oct. 8, 2008, p. 1 http://www.diffuserworld.com/aromaglobATM-essential-oil-diffusernebulizer-p-10.html.

Nebulizing Diffuser, Betterherbs, Oct. 8, 2008, http://betterherbs.serrahost.com/Detail.bok?no=397.

Auroma Nebulizer for the House, Shop.com, Oct. 8, 2008, p. 1 http://www.shop.com/Auroma_Nebulizer_for_the_House_diffuser-46805905-p!.shtml.

Aura Cacia Electric Diffuser House Model, Shop.com, Oct. 8, 2008, p. 1, http://www.shop.com/Aura_Cacia_Electric_Diffuser_House_Model_diffuser-46805768-p!.shtml.

Essential Air Room Diffusers, Leyden House, Oct. 8, 2008, p. 1 http://www.leydenhouse.com/diffusers.html.

http://www.air-aroma.com/diffusers, Mar. 21, 2013.

http://www.prolitec.com/appliances_commercial.htm, Mar. 21, 2013.

http://scentair.com/why-scentair-solutions/, Mar. 21, 2013.

http://www.brandaroma.com/products/, Mar. 21, 2013.

http://www.e2aroma.com/appliances/smart-air-maxi/, Mar. 21, 2013.

http://www.scentaustralia.com.au/index.php/products/scent-diffuser-zephyr, Mar. 21, 2013.

http://www.voitair.com/scent-systems, Mar. 21, 2013.

http://www.fragrancemachine.com/, Mar. 21, 2013.

Spa Room Purifier Assortment with instructions, http://www.sparoom.com/catalog/, webpage, Sep. 1, 2015.

Floracopeia, Inc., S3 Nebulizing Diffuser, User Manual Apr. 2015.

Shenzhen Jing Xin, Sharing Together Pure Aromatic Fresh Air Catalog, Apr. 2015.

* cited by examiner

COMPACT, MOBILE, MODULAR, INTEGRATED DIFFUSER APPARATUS AND METHOD

RELATED APPLICATIONS

This application claims the benefit of U.S. Provisional Patent Application Ser. No. 62/277,343, filed Jan. 11, 2016. This application is a Continuation-in-Part of U.S. patent application Ser. No. 15/297,542, filed Oct. 19, 2016; which is a divisional of U.S. patent application Ser. No. 14/260, 520, filed Apr. 24, 2014, now U.S. Pat. No. 9,480,769, issued Nov. 1, 2016; which is a continuation-in-part of U.S. patent application Ser. No. 13/854,545, filed Apr. 1, 2013, now U.S. Pat. No. 9,415,130, issued Aug. 16, 2016. This application is a Continuation-in-Part of U.S. patent application Ser. No. 15/373,035, filed Dec. 8, 2016; which claims the benefit of U.S. Provisional Patent Application Ser. No. 62/265,820, filed Dec. 10, 2015. All of the following are hereby incorporated by referenced in their entirety.

This application also incorporates by reference: U.S. patent application Ser. No. 12/247,755, filed Oct. 8, 2008, issued Feb. 1, 2011, as U.S. Pat. No. 7,878,418, U.S. Design patent application Ser. No. 29/401,480, filed Sep. 12, 2011, issued May 29, 2012, as U.S. Design Pat. No. D660,951; U.S. Design patent application Ser. No. 29/401,517, filed Sep. 12, 2011, issued Sep. 4, 2012, as U.S. Design Pat. No. D666,706; U.S. patent application Ser. No. 13/854,545, filed Apr. 1, 2013; U.S. patent application Ser. No. 14/260,520, filed Apr. 24, 2014; U.S. Design patent application Ser. No. 29/451,750, filed Apr. 8, 2013, U.S. Design patent application Ser. No. 29/465,421, filed Aug. 28, 213; U.S. Design patent application Ser. No. 29/465,424, filed Aug. 28, 2013; and U.S. patent application Ser. No. 14/850,789, filed Sep. 10, 2015.

BACKGROUND

Field of the Invention

This invention relates to diffusion of essential oils and, more particularly, to novel systems and methods for modularizing diffusers for mobile applications and simplified operation.

Background Art

Mechanisms exist for altering a closed environment such as a room or home with humidity. Likewise, mechanisms exist for removing humidity. Electronic and chemical mechanisms for destroying microbial sources of offensive scents exist. Meanwhile, sprays, evaporators, wicks, candles, and so forth also exist to vaporize and distribute volatile scents, essential oils, alcohols or other liquids bearing scents, and so forth. These may be introduced into breathing air, an atmosphere of a room, or any other enclosed space.

Heating often destroys, or at least changes, the constitution of essential oils. Thus, it has limitations. However, the evaporation rates or atomization rates of essential oils are often insufficient to provide a controllable, sustainable, and sufficient amount of an essential oil into the atmosphere. Thus, wicks having no positive breakup mechanism or no air movement mechanism often prove inadequate.

Meanwhile, mechanisms that seek to copy vaporizers and moisture atomizers often damage surrounding equipment, furniture, and other environs of a space being treated by overspray or settling out of essential oils. Moreover, the continuing "spitting" by atomizers of comparatively larger droplets not only causes damage to finishes on surrounding surfaces, but wastes a substantial fraction of the essential oil.

Essential oils are concentrated sources of aromas or scents. Their extraction from source plants is sometimes complicated, and always comparatively expensive, based on the cost per unit volume of the essential oil. Therefore, colognes, other fragrancing systems, and the like often use comparatively high tractions of diluents for essential oils. They also use synthetic oils and artificial scents that may not replicate the comforting, familiar, and natural essence of essential oils.

By whatever mode, systems to distribute essential oils often waste an expensive commodity while damaging surroundings about their atomizers or other distribution systems. Thus, it would be an advance in the art to provide an apparatus and method for distributing essential oils in as small particles as possible, preferably vaporized or else suspending in air permanently, while protecting surrounding areas. It would be an advance to do so while retrieving and recycling for re-atomization or diffusion any droplets that are larger than those that may be sustained against gravity by fluid dynamic drag or by effectively Brownian motion once discharged into surrounding air.

It would also be an advance in the art to improve diffusers to make them smaller, more compact, and more mobile so they may be used in a particular room, moved from room to room, or even carried in a vehicle. Adding aromas to vehicles has long been the purview of poorly constructed and short-lived, absorbent materials suspended by a tether from a mount of a rear view mirror. Effective selection of scent, duration and intensity of scent, and other desirable controls have been effectively absent. Moreover, the complexities of controls have likewise been a deterrent to rapid and simplified mechanisms for selecting an effective operational cycle.

It would be an advance in the art to provide an integrated control mechanism that effectively limits a number of decisions, and perhaps even choices, simplifying and integrating them into parameters that may be more readily understood selected. In some embodiments, it would be a substantial benefit to a user to have a system that integrates information from a user, translates it into operational characteristics of a diffuser, and automatically sets the controlling parameters without the common trial and error or unknown consequences typically imposed on a user.

BRIEF SUMMARY OF THE INVENTION

In view of the foregoing, in accordance with the invention as embodied and broadly described herein, a method and apparatus are disclosed in one embodiment of the present invention as including a reservoir fitted with an extraction system for drawing out of the reservoir and feeding into a diffuser nozzle. The nozzle may operate as an eductor. In fact, in certain embodiments an eductor may include an injection nozzle feeding into a plenum which plenum feeds through a diffuser nozzle toward an ultimate discharge point or port.

In certain embodiments, a system may include separation or drift chambers. For example, an initial separation chamber may actually be an evacuated space or vapor space near the top of a reservoir. This provides the advantage of the reservoir directly relying on contact accumulation, coalescence by contact between an atomized spray and the content of essential oil in the reservoir.

Separator mechanisms may coalesce out comparatively larger droplets as they either drift into or strike with impact against solid surfaces. Solid surfaces may be naturally occurring walls of conduits, the reservoir, and so forth. However, surfaces may also be made up of baffles simply placed within a conduit or path in order to cause changes of direction, and to receive and coalesce overly large droplets. "Larger" means having too much mass, or rather too great a mass-to-cross-sectional-area ratio to drift indefinitely (e.g., permanently) in air. This may also be expressed as a volume-to-surface-area ratio.

A decrease of radius decreases surface area as the square of radius, while decreasing volume as the cube of radius. Accordingly, there comes a point at which the cross sectional area controlling fluid drag of droplets in air is sufficiently large yet the mass and volume are sufficiently small, that a particle of such size may remain suspended indefinitely in air (e.g., permanently or until evaporated or captured). That is, the drag force resisting drift of the droplet downward under the force of gravity is sufficient to maintain indefinitely the drift of that droplet with the movement of air. Stated another way, the gravitational force is so miniscule as to be irrelevant to the time of drift. Gravity is unimportant. Drift can proceed effectively indefinitely.

Evaporation is an entirely different mechanism. In evaporation, individual molecules of a liquid become individual molecules of vapor. Vapors then abide by Dalton's law of partial pressures and take their place with other surrounding vapors including air, constituted primarily by oxygen and nitrogen. Thus, evaporated portions of an essential oil have performed well their function of distributing into the surrounding air.

Meanwhile, droplets sufficiently small to remain airborne substantially indefinitely, despite gravity, have also achieved their mission to distribute in air. Droplets too large, and therefor too heavy, cannot be sustained in surrounding air against drift downward under the force of gravity. By drifting down these are recaptured. Otherwise they would have become the culprits in waste of essential oils and the damage to surrounding surfaces on which such droplets land.

Thus, in an apparatus and method in accordance with the invention, it has been found that various separators have proven effective to provide several key factors. For example, separation devices provide time. The time of passage or containment of a droplet within a separation chamber provides opportunity for comparatively larger droplets to drift toward any coalescing surface. By coalescing surface is meant a surface upon which overly large droplets may strike and coalesce with one another under the natural surface tension affinity that the essential oil or other material has for itself.

Also, the separation chambers have inlets and outlets offering changes of direction and cross sectional. Moreover, barriers may intercept "comparatively larger" particles by serving as coalescing surfaces. Barriers may also redirect flows, thereby encouraging striking thereof by overly large particles.

Herein we will define overly large particles as particles that are larger, especially those more than an order of magnitude larger in diameter, than self-sustaining (permanently drifting) droplets. Thus, permanently drifting droplets are defined as droplets of an atomized liquid that are sufficiently small that they will not drift consistently downward, especially the height of a room within a day of eight to twenty four hours.

Thus, the finest particles, defined as permanently drifting particles are those whose gravitational acceleration under the force of gravity is insufficient to drift them down before they are swept along with air currents. Of interest also is any droplet that will not descend the height of a room within a day due to the resistance to drifting down by the fluid drag of the surrounding gases, such as room air or air in another confined space, such as a vehicle. As a practical matter, droplets larger than these finest or permanently drifting particles are sufficiently small if they will drift with an airflow and leave with ventilation air. Often, air leaves a room or an enclosed space of a vehicle in a matter of less than an hour.

For example, the American Society of Heating, Refrigerating, and Air Conditioning Engineering (ASHRAE) defines standards for room ventilation. Finest particles will necessarily be drifting with the flow of air and will leave a room before they have substantial opportunity to drift to the floor. Moreover, because room air is exchanged so frequently, typically more than once per hour, particles that are an order of magnitude larger than the finest particles also fit within the definition of comparatively smaller particles. In other words, these stay aloft for sufficient time to be swept out with the circulation of room air or vehicle air.

What is now available is a compact system to accomplish atomization and subsequent separation of the comparatively larger particles that can drift to the ground in less than an hour or less than an air exchange time. The size may vary with temperature and with the specific gravity (density compared to the density of water) of a particular essential oil.

Thus, an apparatus and method in accordance with the invention may rely on a compactly packaged, system for a reservoir, a motor and pump system, and one or more separation mechanisms. They may include drift chambers in the flow path. The separation mechanisms provide drift time and a smooth flow separation mechanism for comparatively larger particles to drift toward and coalesce against solid surfaces.

In one embodiment, a jet entrains a certain amount of an essential oil to be atomized. This jet, proceeding out of the jet nozzle or injection nozzle (which initiates and creates the jet), passes through a receptacle or well. The well is drawing the essential oil out of the reservoir, through a tube into that receptacle.

The jet of air passing through the essential oil entrains a certain portion thereof, or entrains an essential oil at a rate and with sufficient energy to strip droplets from the surface of surrounding essential oil. It ejects those droplets by a jet through a diffuser nozzle.

Of course, according to the laws of physics and engineering, droplets are generated in a variety of sizes. Initially, the largest of the comparatively larger droplets will not be able to make the turn required to reverse direction. Reversal is required in order to pass back out through the cap and a channel in the cap that exits the vapor space above the reservoir.

By a reservoir is indicated a supply, or a container for holding a supply, of an aromatic substance, such as an essential oil. By a diffuser is meant a system for atomizing and distributed comparatively smaller particles, including finest particles as defined hereinabove, and suitably fine particles that are within about an order of magnitude of the same diameter or radius as finest particles.

A jet is defined as in engineering fluid mechanics. A jet represents a flow of fluid having momentum, and passing through another fluid which may have the same or a different constitution. Thus, an air jet may pass through a surrounding oil. An air jet may pass through surrounding air. A significant feature of a jet is that it passes fluid having momentum through another fluid having a different specific momentum. Accordingly, momentum is exchanged between the environment and the jet, causing the jet to grow in size as a "plume." A plume will decrease in velocity as the momentum is distributed among more actual material (mass).

An eductor is a specific type of fluid handling mechanism. An eductor is a system in which a jet of a first constitution is injected into another fluid, typically of a different constitution. The momentum from the first jet is sufficient to cause the surrounding fluid entrained by the jet to continue as a plume of mixed constitution.

Herein, an eductor mechanism is created in which a jet, the source of that jet, and the surrounding environment into which the jet is injected are passed through an aperture in a nozzle. Any portion of the jet that exceeds the effective diameter or maximum dimension across the nozzle cannot pass therethrough, and thereby must recirculate back to be re-entrained in the jet, or to some other disposition.

A diffuser is in some respects an atomizer, but has the specific objective of producing finest fluid particles or droplets. Accordingly, a diffuser system includes not just an eductor but separation chambers, sometimes distinct separator structures. All are calculated to remove comparatively larger droplets, leaving only finest droplets and those within an about an order of magnitude thereof. Again, finest droplets or particles and comparatively larger particles have been defined hereinabove, in terms of their fluid dynamic behaviors. Those behaviors are defined by well established engineering equations. Therefore, all those equations are not repeated here. One may refer to textbooks and papers published on jets, atomization, fluid mechanics, two-phase flow, entrainment, plumes, and the like to obtain the details of the physics, the flow fields, the operational parameters, and governing equations for these phenomena.

Vapor space in a reservoir is defined as a portion of the volume of a reservoir container that contains other than predominantly the liquid for which the reservoir exists. That is, the vapor region actually contains air, a certain amount of the evaporated essential oil, according to Dalton's law of partial pressure in chemistry, and a certain quantity of drifting droplets in transit.

In certain embodiments of an apparatus and method in accordance with the invention, a reservoir may be fitted with an eductor injecting, through a diffuser nozzle, an entrainment jet containing both air, as the driving fluid, and atomized particles or droplets of the essential oil.

Mass flow rate is equal to an area times the velocity of material passing through that cross sectional area, multiplied by a density of the material flowing. Volumetric flow rate is simply a velocity of the flow rate multiplied by the cross sectional area through which that flow passes.

Whether looking at mass flow rate or volumetric flow rate, area is a controlling parameter. Increasing area, while keeping the volumetric flow rate constant, requires that the velocity slow down. Accordingly, in order to slow the velocity, area is increased. The result of a change in velocity is to permit more time for comparatively larger droplets to drift out of their entraining airflow toward any adjacent wall, baffle, or the like.

Accordingly, it has been found that diffuser systems or diffusion system in accordance with the invention, operating with the structures and fluid mechanisms in accordance with the invention, provide three valuable benefits not found in prior art systems. First, comparatively larger droplets do not exit the discharge port and drift down upon surrounding surfaces. Second, this effectively diffuses and controls, without heating, the amount of the essential oil diffused in order to provide a specific level of scent that is pleasant and effectively as strong as desired (controlled), without being overly strong.

Third, oil use required for a level of scent within a treated space has been shown to be much more efficient. That is, usage rates of less than half to a third of conventional systems result. Sometimes less than about one eighth to one tenth of conventional usage has resulted in systems in accordance with the invention.

In summary, the treated space has the properly controlled amount of the essential oil to provide the aroma and ambiance desired. Compared to prior art systems, whose rate of use is much greater, the essential oils are more efficiently used. Furniture and other surfaces are not damaged, sticky, or unsightly from comparatively larger particles drifting down onto them.

In various embodiments, a compact, integrated system may be placed within any arbitrary base or housing. It has been found that a reservoir may be fitted into virtually any décor.

Meanwhile, only electrical power crosses to the system from the arbitrary base. This results in pleasant possibilities for design, along with compactness, uniformity, and convenience of integration.

In addition, a system in accordance with the invention may integrate the duty cycle parameters controlling the time that a diffuser is on, the time that it remains off between "on times," and the intensity or mass flow rate of air passing through the diffuser. In one embodiment, a system and method in accordance with the invention may rely on translated, human-understood, simplified parameters such as high or low intensity, the size of a volume to be treated, such as a small, medium, or large volume, and a total time during which the system will operate in its on-again, off-again, duty cycle.

To this end, a controller may include an integrated circuit that provides a user with all the calculations to control times, duty cycles (percentage of total time during which the device is actually operating), and so forth. These may permit one to choose and set user-understood control objectives appropriate to comply with the comparative space, intensity, and total duration of time during which the system will operate or continue to "cycle."

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 1 is a partially exploded frontal perspective view of one embodiment of a diffuser system in accordance with the invention;

FIG. 2 is an exploded, perspective view thereof;

FIG. 3 is an exploded, perspective view of the diffuser and reservoir portion thereof;

FIG. 4 is an exploded, perspective view of the base portion thereof, including the power pack and motive (motor and pump) section;

FIG. 5 is a frontal, upper quarter, perspective view of the assembled system;

FIG. 6 is a lower quarter perspective view thereof;

FIG. 7 is a top plan view thereof;

DETAILED DESCRIPTION OF THE PREFERRED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 1:
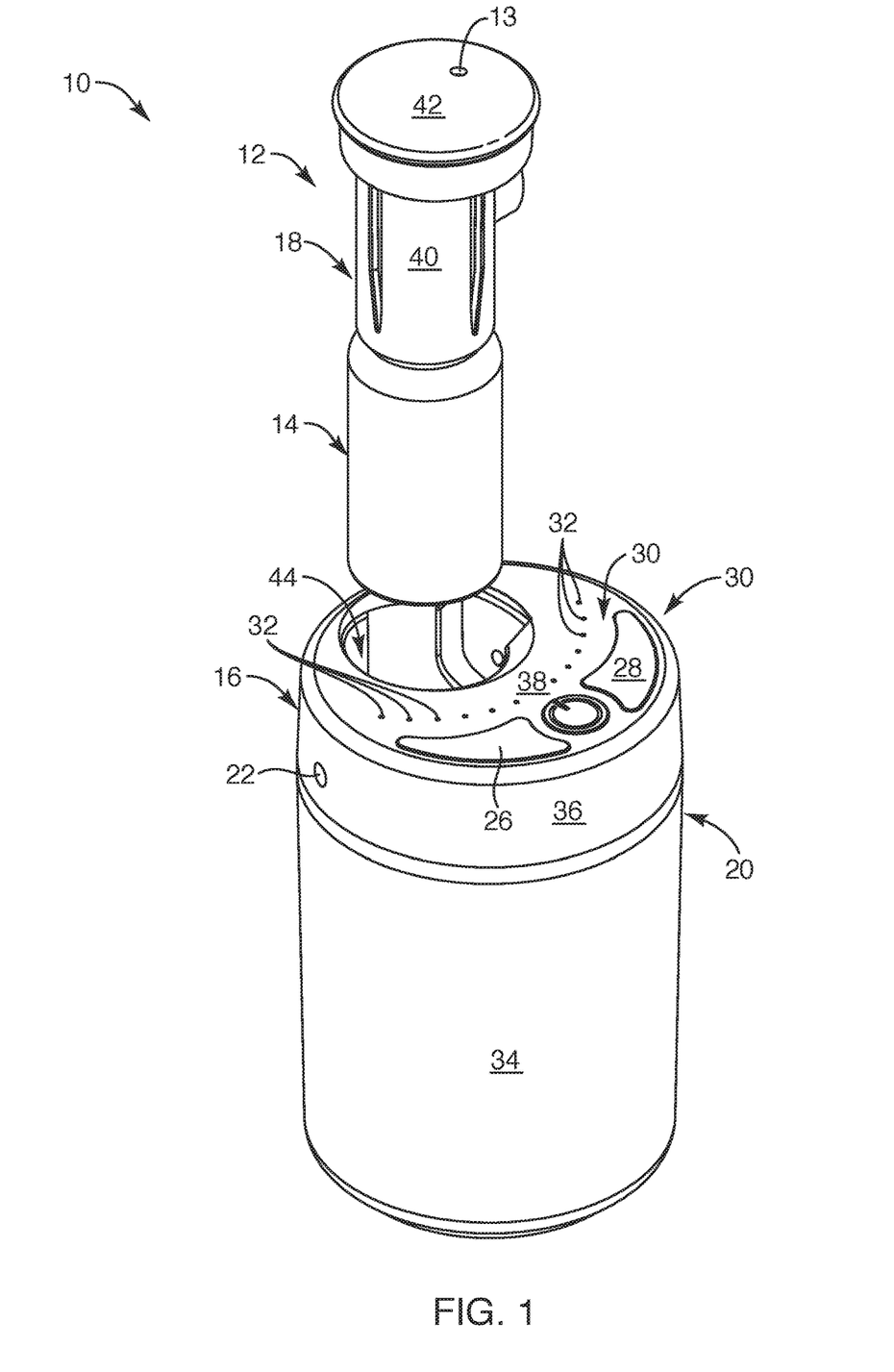
Figure 2:
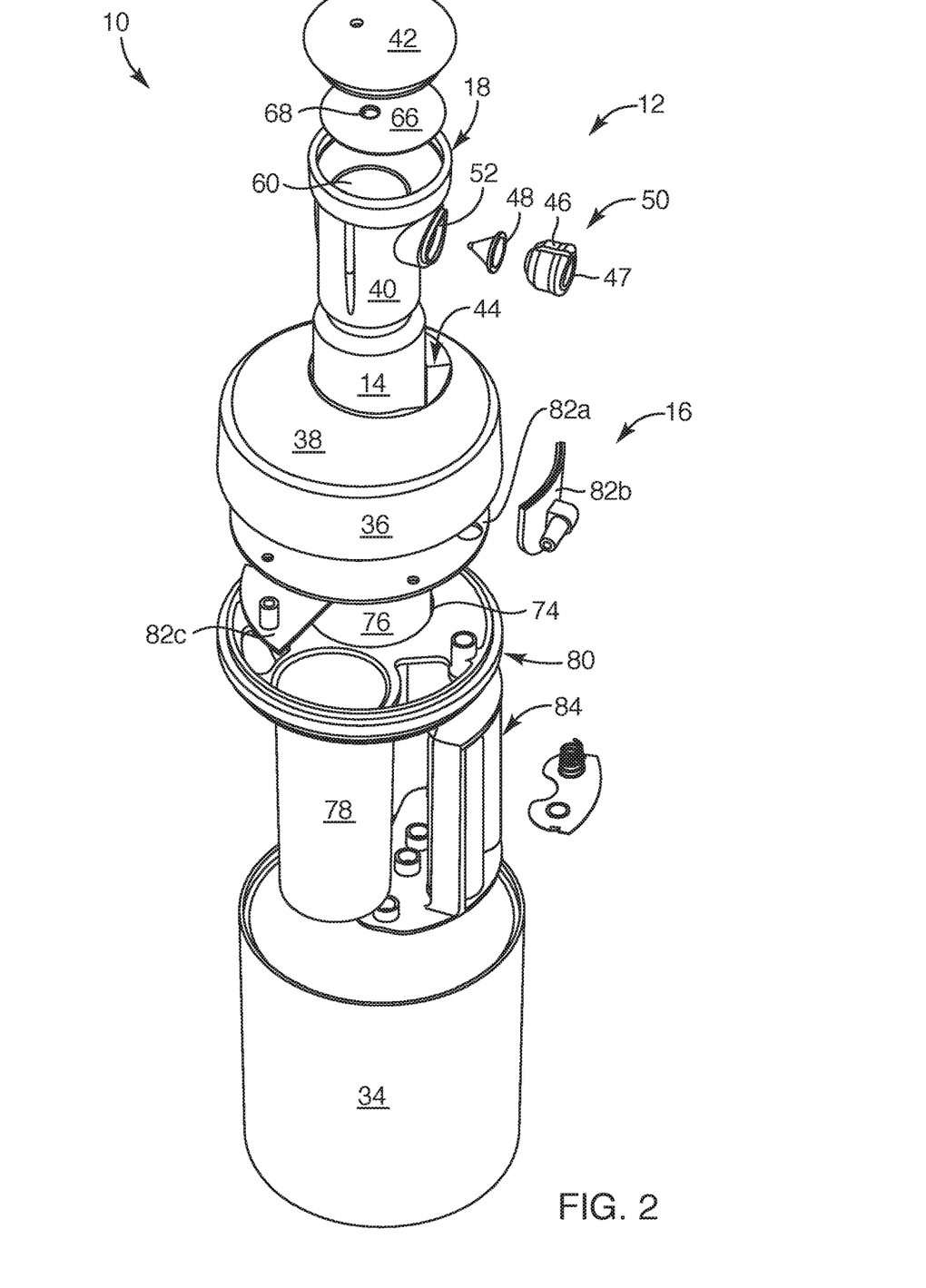
Figure 3:
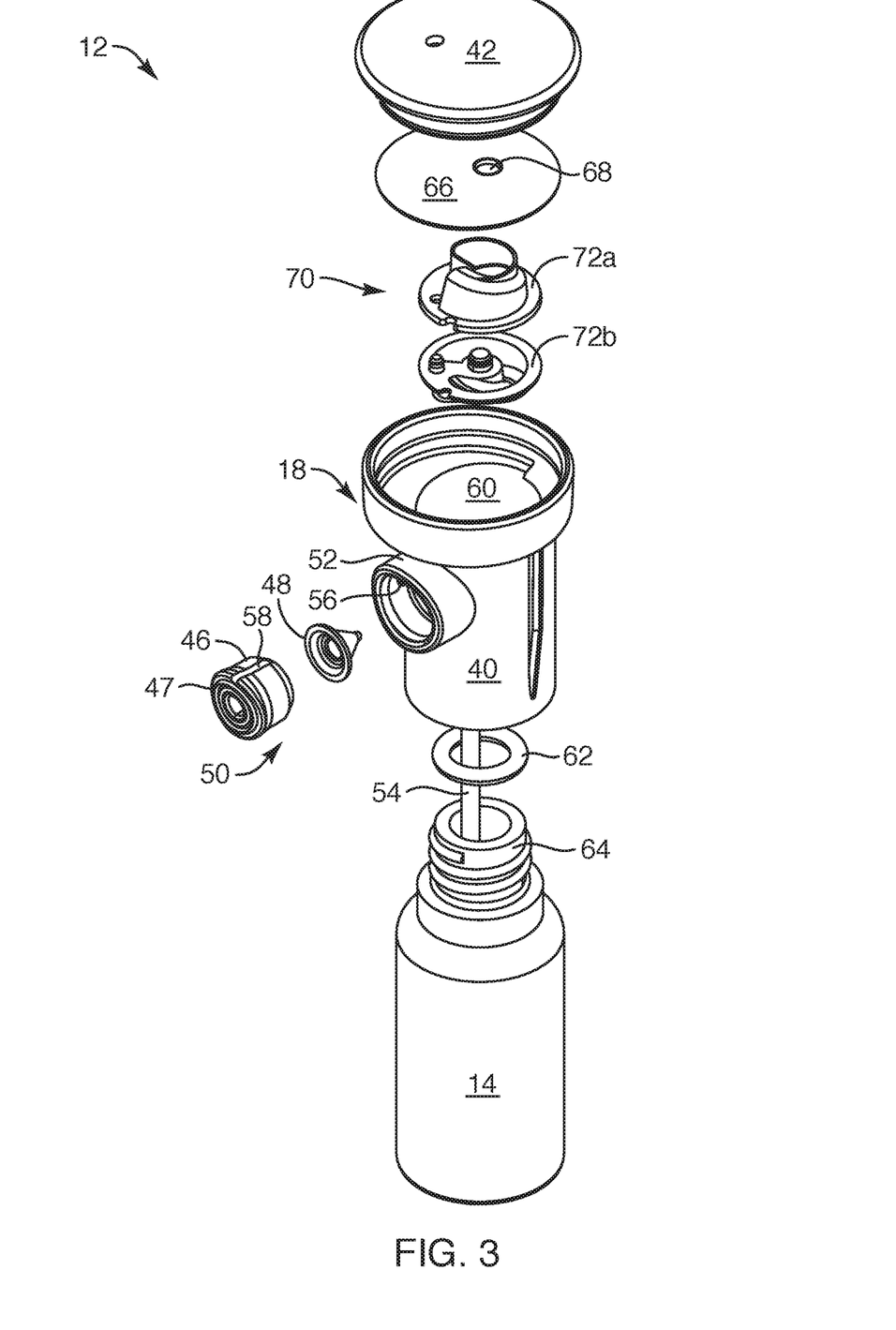
Figure 4:
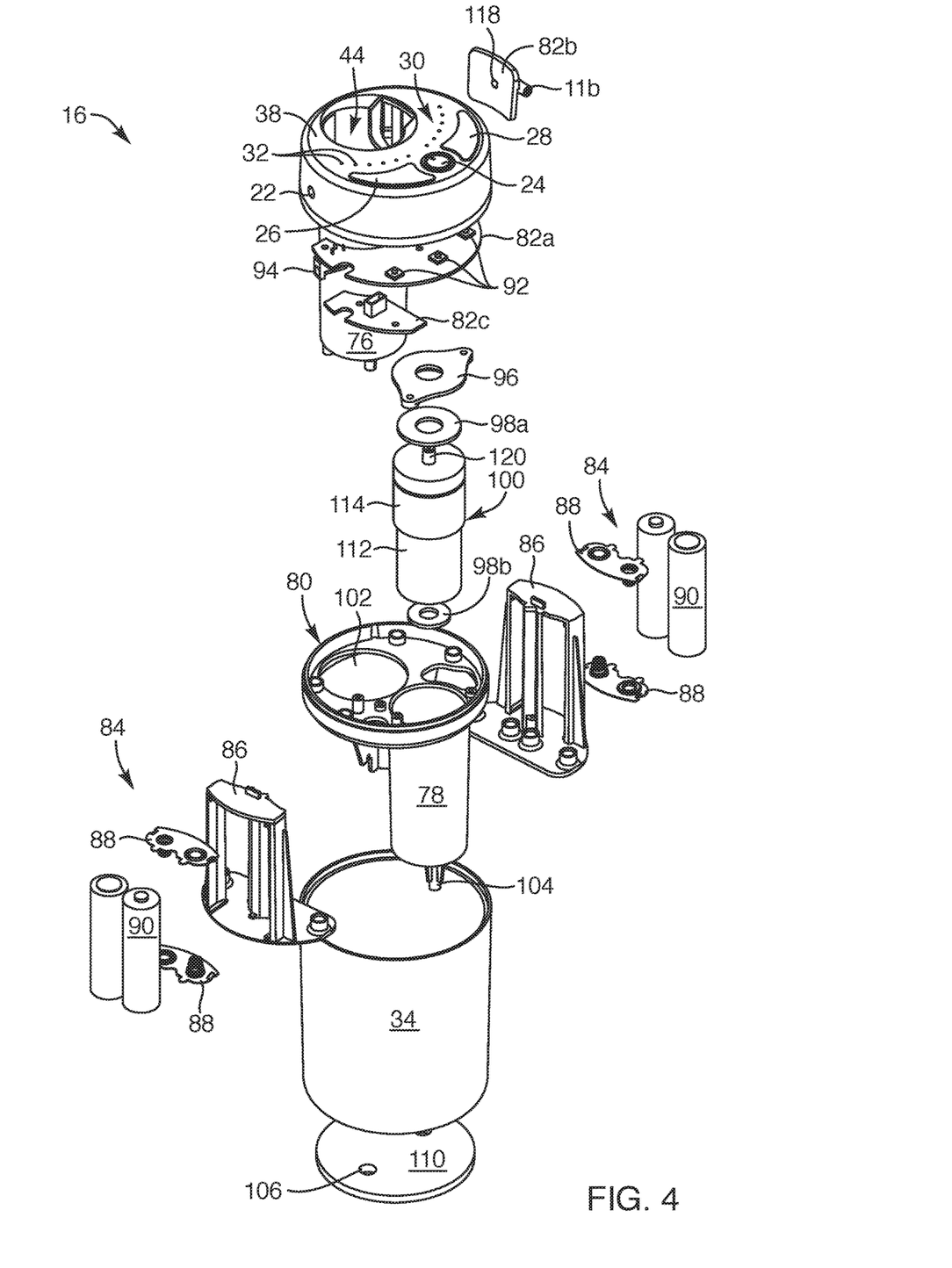

Referring to FIG. 1, while also including FIGS. 2 through 4, as well as FIGS. 1 through 13 generally, a system 10 in accordance with the invention is constituted by a diffuser portion 12 or diffuser 12 attachable to a reservoir 14, such as a bottle 14 or the like. The diffuser 12 and reservoir 14 fit within a base 16. In the illustrated embodiment, the diffuser 12 is sized or defined by a housing 18. Likewise, the base 16 may be defined in its outer envelope, where envelope represents its outermost boundaries, defining dimensions such as length, diameter, and an overall volume that is substantially cylindrical in shape. The housing 20 may include a power port 22. The power port 22 receives electrical power from an outside source. Notwithstanding the base 16 may include electrical power by way of portable batteries, the power port 22 in some embodiments provides for charging of batteries stored within the base 16. In other embodiments, the power port 22 provides for electricity to drive all the systems within the base 16, whether or not batteries are included within.

The button 24 in the illustrated embodiment provides a multi-functional button 24. In one presently contemplated embodiment, the button 24 may be depressed in order to power up the system 10. Logic built into the operation underlying the button 24 may also provide for additional functionality by multiple pushes of the button 24. For example, in one currently contemplated embodiment, the button 24 when depressed a single time turns on power of the system 10 at a first level, such as a high or low volumetric flow rate of air through the system 10. Typically, it may be preferable to default to powering on at a comparatively low intensity or flow rate of air.

Meanwhile, pushing the button 24 twice engages an alternative mode, such as a higher volumetric flow rate. Additional modes (volumetric flow rates) may be engaged with additional depressions or pushing of the button 24 in comparatively quick succession. By quick succession means that mere seconds elapsed between adjacent actuations (pushing) of the button 24. Ultimately, a final maximum number of pushes of the button 24 will result in turning the system 10 off. For convenience, it has been found that a user benefits from simplicity. Accordingly, in one embodiment a single push activates the system 10, powering it on in a comparatively low volumetric flow rate mode. Two pushes or actuations result in a high volumetric flow rate mode. Three pushes result in returning to an off position.

In yet other embodiments, a first push results in positioning it at a low mode, a second push at any subsequent time results in an operation in a high volumetric flow rate mode. Meanwhile, a third push at any time results in an off condition at which no power is provided to operate the system 10.

By saying no power, this indicates that no mechanical motive power. This does not exclude the minor amount of power required for controls. In some modes, all power may be shut off, in others, control power may remain on for operating electronics at comparatively low amounts of current draw.

A button 26 may control a space, area, or other designation of the volume of air to be treated. Typically, area or volume is a concept that a user can rapidly understand. However, the reality is that the system 10 does not actually know or interpret area, but rather adjusts a duty cycle. Thus, by selecting a space size, floor area, room volume, or the like, a user may simply select small, medium, large, or some other designation.

Again, the button 26 may vary from about one percent to about 100 percent duty cycle. Duty cycle may be defined two ways. The simplest way to understand duty cycle is that a duty cycle is a percentage of total elapsed time during which the system 10 operates to diffuse an essential oil or other content used to condition space. Typically, essential oils, other fragrances, mixtures, and so forth may fill the reservoir 14. The diffuser 12 draws out, atomizes, sorts, and diffuses the smallest possible particles and vapors from the reservoir 14. The diffuser 12 returns comparatively larger droplets to the reservoir 14 for recycling.

In one embodiment, a system 10 may have preprogrammed settings. For example, selecting a comparatively small area, when the switch 24 or button 24 is set at a low volumetric flow rate mode may result in about a one percent duty cycle. If the space control button 26 or area button 26 is set for a small region, while the volumetric flow rate control button 24 is set at a high rate and mode the duty cycle may be about 5 percent. A one percent duty cycle corresponds to about six seconds of operation for an elapsed time of six minutes. Similarly, a duty cycle of about five percent will result from a run time of about six seconds out of each two minutes. Since the operational times are comparatively small compared to elapsed time, whether the total elapsed time or a delay time between operations will be used is not a substantial difference. As duty cycles increase, the difference between total elapsed time and a delay time between operation may be more significant.

In one embodiment, a medium space or area setting with a low volumetric flow rate may be met with about a ten percent duty cycle. If the same area or volume is handled at a high volumetric flow rate, then about 20 percent for a duty cycle is appropriate. Similarly, a large area or volume setting at a low volumetric flow rate may be served by about a 40 percent duty cycle. Meanwhile, the same area or volume at a comparatively high volumetric flow rate may be served by about a 66 percent duty cycle. Again, duty cycle is typically defined as the percentage of operational time out of total elapsed time. However, duty cycle may also be defined by a run time compared to a rest time therebetween. By using the former, duty cycle will always be a value between zero and 100 as a percent or between zero and one as a fraction.

The total time button 28 represents the total amount of time that a user desires to leave or permit the system 10 to continue to cycle on and off. Thus, the button 28 may be considered an occupation time button 28. This button 28 thus protects against the system 10 continuing to operate when a room or vehicle has been vacated. Thus, the button 24 allows a setting of some maximum number of minutes or hours that the system 10 will continue to cycle. This saves essential oil, power, and wear of the system 10. It may also save the environment of a comparatively small volume of space from being overwhelmed by scent. For example, a system 10 left unattended and operating indefinitely in a vehicle that has been parked and closed up may result in uncomfortable levels of scent.

Thus, in one embodiment, an individual may depress the button 28 multiple times to indicate the number of hours, or fractions of hours that the system 10 will remain cycling. Meanwhile, the button 26 may reflect directly, and select, a user's concept of the volume or floor space being treated. Meanwhile, the power button 24 may select an "on" condition, in a comparatively higher or lower volumetric flow rate mode.

It has been found that users prefer and are less intimated by a limited number of options. Too many options create a mental programming problem. Thus, it has been found that times ranging from about half an hour to an hour, two hours, four hours, and either six or eight hours meet the needs of most people. As a default, in the illustrated embodiments, beginning with a half hour, times double except for the last time, which is six hours rather than eight.

Indicators 32 may be represented by lights. For example, on each side of the power button 24, or mode button 24, an indicator of high and low. That is, a light of one color may represent a low volumetric flow rate, while a light of another color may represent a high volumetric flow rate. In other embodiments, the words "low" and "high" may be backlit by lights on one side and the other, respectively, of the button 24. Similarly, the indicators 32 above or near the space button 26 or area button 26 may indicate by words, colors, backlighting, or both, the small, medium, and large settings for the treated space. Likewise, the duration button 28 or total time button 28 may be identified by lights, colors, numbers, or a combination thereof. The setting at which the button 28 is placed represents a total elapsed time.

Together, all of the buttons 24, 26, 28, and the indicators 32 may represent a system of controls 30. The controls 30 provide for inputs by a user through the buttons 24, 26, 28, controlling on/off and volumetric flow rate (intensity), space (size) to be treated, and the total time of cycling operation, respectively. The indicators 32 may be implemented in individual lights, which may vary by color or vary in color to provide indications thereby. In other embodiments, the indicators 32 may simply be transparent or translucent areas having words that are backlit by light emitting diodes (LED), or the like to be discernable to a user.

The system 10 with its three principal subsystems of a diffuser 12, a reservoir 14, and a base 16 divides functionalities therebetween. For example, the housing 18 of the diffuser 12 represents a comparatively self-contained system that needs to access the reservoir 14 holding contents to be diffused. The diffuser 12 needs to access the base 16 for a supply of pressurized air to operate the diffuser 12.

All these components have need to be packaged or contained. For example, the housing 20 of the base 16 may include a barrel 34 or barrel portion 34 that is closed by a cap 36 on the top thereof. The cap 36 may have distributed on its top 38 or top surface 38 the various controls 30, including the buttons 24, 26, 28, and the indicators 32. Accordingly, the material of the cap 36, and specifically the top 38 thereof, may be formed of a suitable material for transmitting light through transparency, translucence, or apertures. In other embodiments, lights for indicators 32 may be embedded in the top 38 of the cap 36.

Likewise, the housing 18 of the diffuser 12 may be formed of a barrel 40 and a cap 42 enclosing it or closing it. In the illustrated embodiment, the entire diffuser 12 with the reservoir 14 attached may fit through an aperture 44 or into a silo 44 in the base 16. This arrangement provides for ready access to the reservoir 14 by a user. Thus, no electrical power need be affected, and no other components need be affected, by removal and replacement of a reservoir 14 of essential oil or other content.

Likewise, the entire diffuser 12 operates, to a certain extent, as a cap 12 for the reservoir 14. Because no major effect results to the housing 20, a user may actually maintain multiple diffusers 12 as caps on various reservoirs 14. Thus, the diffusers 12 may actually serve as caps on a quasi-permanent basis for various reservoirs 14 of selected scents.

Referring to FIGS. 2 through 4, while continuing to refer generally to FIGS. 1 through 13, the diffuser 12 may include a fitting 46 or fixture 46 responsible to interface between the diffuser 12 and the base 16. The diffuser 12 relies on the fitting 46 or fixture 46 to provide a seal 47 or sealing surface 47 that registers, and connects in fluid communication with a source of pressurized air to operate the diffuser 12.

Referring to FIG. 3, as well as FIGS. 2 and 4, and FIGS. 1 through 13 generally, the fitting 46 may seal against the base 16 by the seal 47, and likewise seal against the nozzle 48 or air nozzle 48. The air nozzle 48, in turn may seal against the barrel 40 or a portion of the barrel 40 to form an integral portion of an eductor system 50. The eductor system 50 is contained within its own housing 52 extending from a wall of the barrel 50. Meanwhile, a tube 54 or line 54 extending down into the reservoir 14 secures into the eductor system 50 as described in detail in various of the references incorporated herein by reference.

A key 56 in the housing 52 fits into a slot 58 in the fixture 46 or fitting 46. Thus, alignment is provided for improving tolerances and fit. For example, the seal 47 may be shaped, along with the fitting 46, to seal against a curved surface inside the base 16.

The chamber 16 within the barrel 40 receives educted spray of pressurized air along with entrained content from the reservoir 14. The details of this eduction and atomization are described in great detail in the various other references incorporated hereinabove by reference.

The diffuser 12 may engage a seal 62 between the barrel 40 and the neck 64 of the reservoir 14. In this way, a vapor-tight and liquid-tight seal is formed by the seal 62 against the neck 64 of the reservoir 14 and a corresponding surface inside the barrel 40. Each may be threaded appropriately with matching threads to engage by a few quick turns or rotations of the reservoir 14 with respect to the barrel 40.

In some embodiments, a baffle 66 or separator 66 may be used. However, the chamber 60 provides a first separation chamber 60 for separating out comparatively larger droplets from comparatively smaller droplets of the atomized content from the reservoir 14. Again, this is described in detail hereinabove and in the references incorporated herein by reference. Meanwhile, the baffle 66 or separator 66 provides an additional change of direction and creates an additional separation chamber or drift chamber within the cap 42. Thus, the general area or volume of the chamber 60 may operate as one separator, or separation chamber 60. The baffle 66 or separator 66 with its aperture 68 passing into the region enclosed by the cap 42 operates as a final separation chamber. A micro cyclone 70 formed in two halves 72a, 72b, which snap together, operates as a third separator 70. Once more, the details and operation of the micro cyclone 70 are included in the references incorporated hereinabove by reference.

A micro cyclone 70 may be formed to conduct flow from the pressurized air passing through the eductor system 50 into the chamber 60. Typically, the micro cyclone 70 may include a circumferential passageway extending from about 45 to about 360 degrees of circumference. The effect of a micro cyclone 70 is to provide a longer path and a more consistent path therethrough subjecting the liquid droplets in an entrained flow of air to centripetal forces. Those forces effectively drive comparatively larger droplets having greater mass and a reduced cross-sectional-area-to-mass ratio toward the outside wall (radially outward) of the micro cyclone 70. At that outermost radius of flow in the micro cyclone 70, droplets coalesce against a solid wall and thereby agglomerated to flow back into the reservoir 14.

Referring to FIG. 4, as well as FIGS. 2 and 3, and FIGS. 1 through 13 generally, the base 16 may be constructed to include an aperture 44 or silo 44 receiving the reservoir 14 and diffuser 12. Likewise, an aperture 74 receives a sleeve 76 for receiving the reservoir 14. Inasmuch as the base 16 charges the diffuser 12 with pressurized air, separation of components permits sealing against intrusion by air, essential oil or other contents of the reservoir 14, or intrusion by pressurized air bearing droplets of liquid.

Accordingly, a sleeve 78 may be formed as a separate component, or may be molded as an integral and homogeneous portion of a collar 80. The collar 80 fits between the barrel 34 of the base 16 and its cap 36. Thus, the collar 80 becomes a platform readily removable from the barrel 34. Between the collar 80 and the cap 36, sufficient space provides for various substrates 82. The substrates 82 may actually be printed circuit boards 82 in some instances. Typically, the substrates 82 provide mounting surfaces for electrical and electronic components corresponding to the controls 30. Thus, lights, LED's, buttons, micro switches, circuits, and the like may be built on the substrates 82.

In some embodiments, power packs 84 may be integrated, but need not be. They may include racks 86 and connectors 88 for electrically connecting batteries 90 to one another and to the electronics on the substrates 82.

Wiring and circuitry may be included as appropriate to connect power from the batteries 90 to various controls and switches. In one embodiment, micro switches 92 may actually be positioned to be actuated by the buttons 24, 26, 28 on the top 38 of the cap 36.

Similarly, a substrate 82, exemplified by the substrates 82a, 82b, 8c may include various components. A jack 94 or socket 94 may receive a plug of some appropriate type for transferring electrical power instead of using power packs 84, or into the power packs 84, and specifically to the batteries 90 for recharging.

A pump module 100 may include a motor portion 112 and a pump portion 114. The motor 112 uses power from the power pack 84 or directly from a line into the power port and jack 94. In fact, a power pack 84 may be dispensed with in order to reduce cost. In such an embodiment, the power port 22 receives a plug into the jack 94 or socket 94 that powers the system 10 from some other power supply such as A/D or A-to-D converter. Similarly, the system 10 may be powered by a line originating in a vehicle from a power source, such as a socket commonly available for a lighter, or other electrical devices, including USB sockets, and the like.

The pump module 100 may be secured in the barrel 78 by a retainer 96. Meanwhile, seals 98a, 98b may seal the pump module 100 within the sleeve 78. In this way, air may pass to the fitting 116 or tube 116 and thereby to the substrate 82b. The substrate 82b may be a portion of a wall, or may simply be positioned near a wall of the sleeve 76 containing the reservoir 14. Thus, when the diffuser 12 is set into the aperture 44 or silo 44 of the base 16, the seal 47 on the fitting 46 slides into a sealing engagement with the substrate 82b.

Meanwhile, an aperture 118 in a substrate 82b connects to a tube 116 or fitting 116, which may be extended between the tube 116 by flexible tubing connecting to the outlet 120 of the pump portion 114 of the pump module 100. In the references incorporated herein by reference, various embodiments of flow paths are discussed for drawing air over the motor module 112 or motor portion 112 and into the pump portion 114, thereby cooling the motor 112 and the overall pump module 100 by the air that will eventually be pushed through the outlet 120 and into the nozzle 48.

The pump module 100 may be juxtaposed to an aperture 102 in the collar 80. The aperture 102 receives the sleeve 76 or container 76 that receives the reservoir 14 and diffuser 12. However, the sleeve 78 may actually be molded as an integral and homogeneous part of the collar 80, thereby containing the pump module 100. In fact, an O-ring seal may seal the module 100 against the walls of the sleeve 78.

Meanwhile, a foot 104 may support the sleeve 78. In certain embodiments, the foot 104 may be a tubular passage 104 that fits into or against an aperture 106 in the floor 110 of the housing 20 of the base 16. Thus, the foot 104 may actually receive air from outside the system 10, through an aperture 106. To effect this, the shape, texture, or various projections on the underside of the floor 110 may be essential or effective to provide space for drawing air through an aperture 106 and foot 104 into the sleeve 78.

Thus, the air passed into the sleeve 78 may pass around the motor portion 112 and into the pump portion 114 to eventually be pressurized. It may be injected through the outlet 120 into the flexible tubing connected to the tube 116, feeding pressurized air through the aperture 118 and thence through the seal 47 and fixture 46 to feed the nozzle 48.

Referring to FIGS. 5 through 12, the assembled system 10 is illustrated with its components largely contained with its outer envelope. The result is a system 10 that fits within a cup holder of a vehicle, sits comfortably on a shelf, may be moved or even carried with an individual, for use in various different spaces during a day.

For example, a system 10 in accordance with the invention may transport in a bag, box, or other container to be used at home, in a vehicle, and in an office. Power may be provided through the power port 22 through an electrical connection 94 directly to a motor portion 112, or by way of a power pack 84 containing batteries 90.

Figure 5:
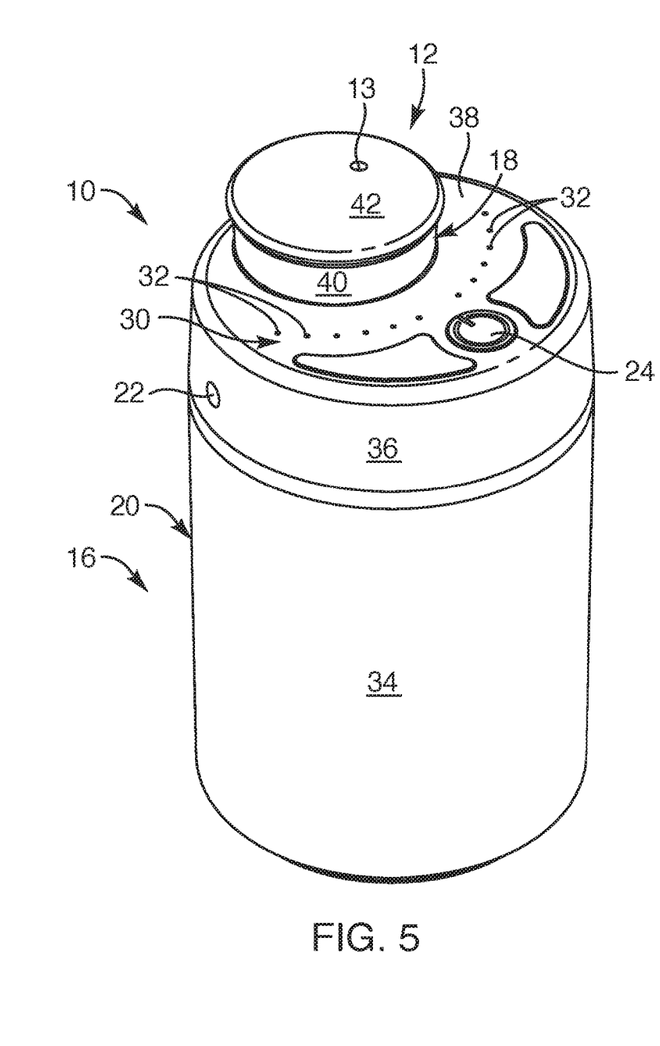

Referring to FIG. 5, while continuing to refer generally to FIGS. 1 through 13, the upper perspective view illustrates how the exit aperture 13 on the cap 42 of a diffuser 12 is the only component or constituent that needs to have access to the outer environment. Nevertheless, by providing a portion of the barrel 40 extending above the top 38 of the cap 36, a user may easily grip the diffuser 12 in order to replace a reservoir 14 or refill the reservoir 14.

Figure 6:
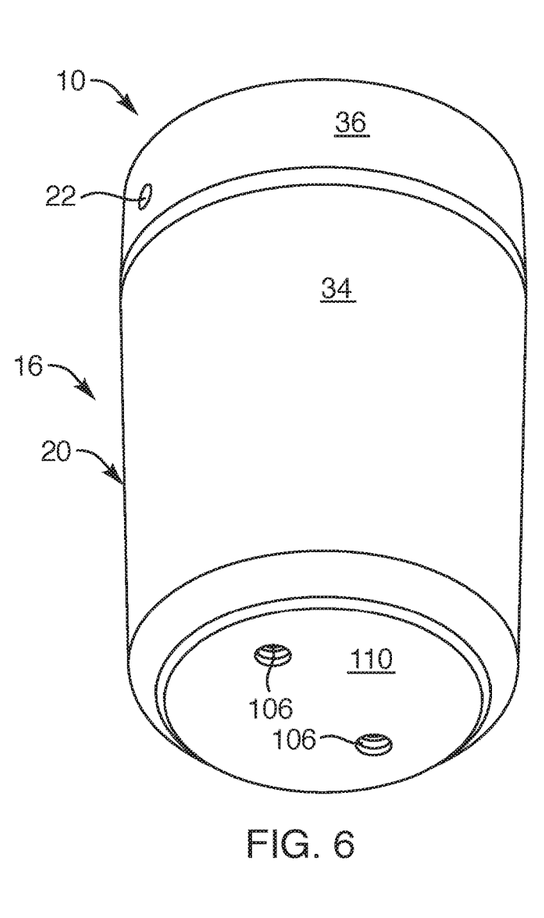

Referring to FIG. 6, one will note that the apertures 106 may be set in positions to register with the foot 104 of the barrel 78, or the foot 104 may simply space the barrel 78 above the floor 110. The apertures 106 may both feed air into the region around the foot 104, and pass that air on into the barrel 78 by any suitable route. In fact, in some embodiments, air may actually be drawn into the barrel 78 by way of passage through the entire volume of the barrel 34 of the base 16.

Figure 7:
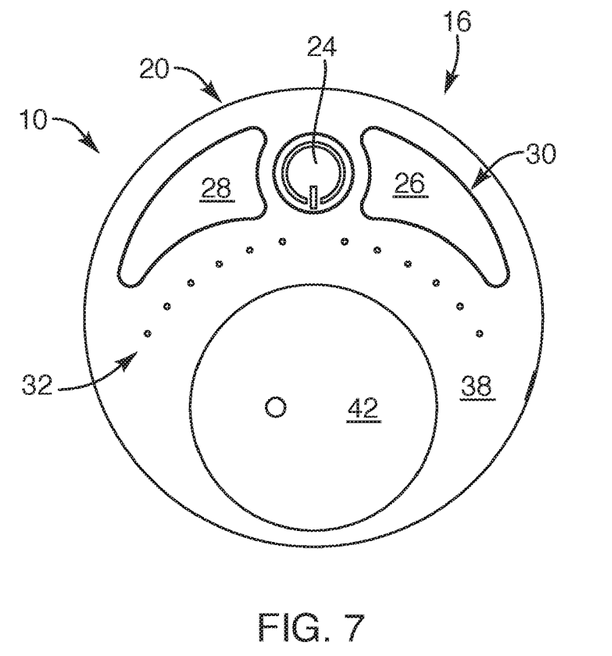
Figure 8:
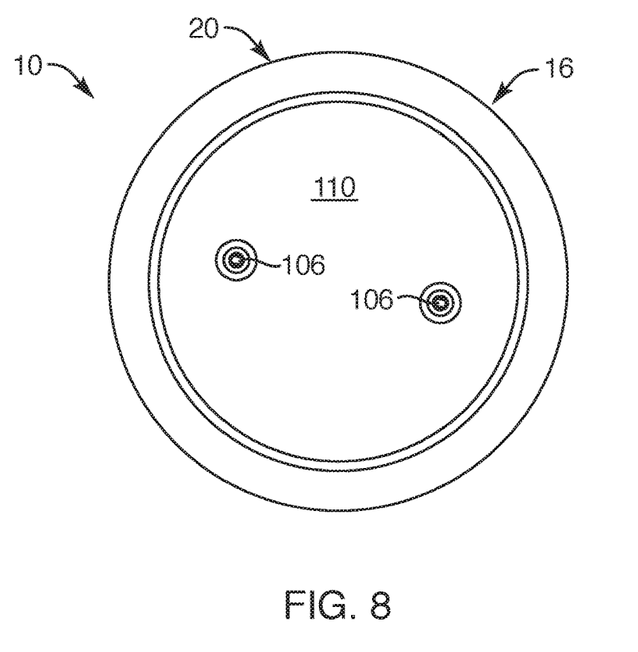
FIG. 8 is a bottom plan view thereof.
Figure 9:
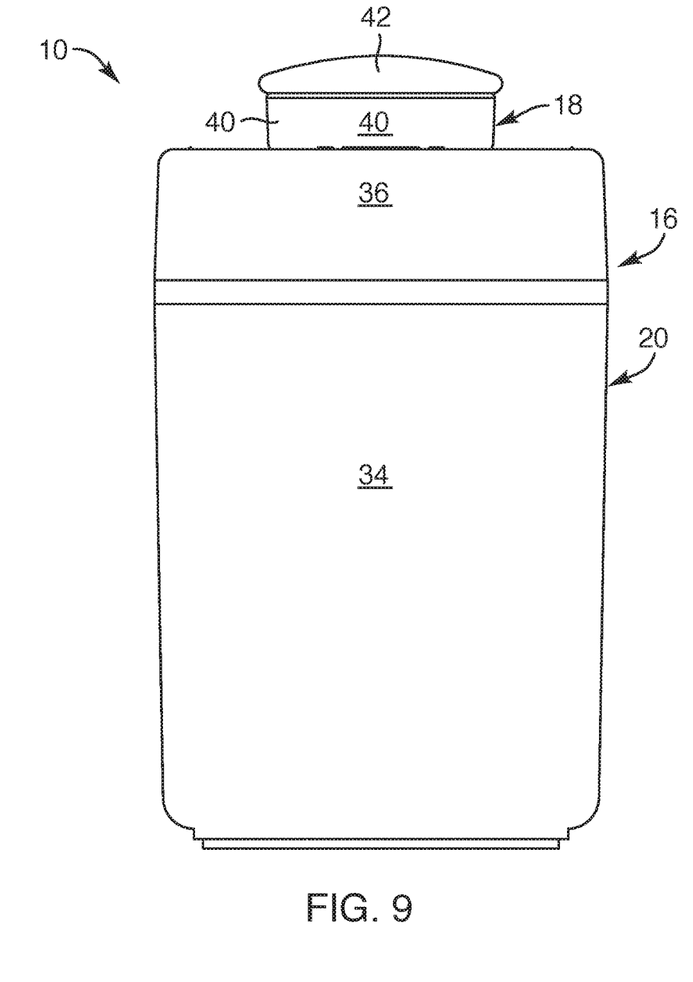
FIG. 9 is a front elevation view thereof.

Referring to FIGS. 7 and 8, while continuing to refer generally to FIGS. 1 through 13, the top plan view of FIG. 7 illustrates a position of the cap 42 of the housing 18 corresponding to the diffuser 12. Similarly, the top 38 of the cap 36 of the housing 20 corresponding to the base 16 displays the control systems 30 including the buttons 24, 26, 28 and indicators 32. The shapes and sizes of the buttons 24, 26, 28 are selected primarily for convenience.

For example, the power button 24 that controls volumetric flow rate as well is centered to be collinear with a diameter through the center of the cap 42. Meanwhile, the button 26 on the left is thus easily accessible through most of a quarter of the circumference, and by simply touching somewhere near the left side of center. Similarly, the duration button 28 may be accessed just to the right of the power button 24. Thus, one advantage of the side elevation of the cap 42 above the top 38 of the cap 36 of the housing 20 about the base 16 is that it serves to orient a user without having to focus, nor indeed even see the buttons 26, 28.

Of course the indicators 32 may be visible on the top 38, or may be distributed somewhere around a side of the cap 36. Nevertheless, this has been found suitable, particularly when a user is above the system 10. That is true more particularly when the system 10 is installed in a cup holder in a vehicle. The indicators 32 are easily visible, and may include readable words indicating the status of the volumetric flow rate according to the power button 24. This is likewise so for the volume or amount of space conditioned, as set by the space button 26, and the total duration of operations before complete shut down, as set by the button 28.

Figure 10:
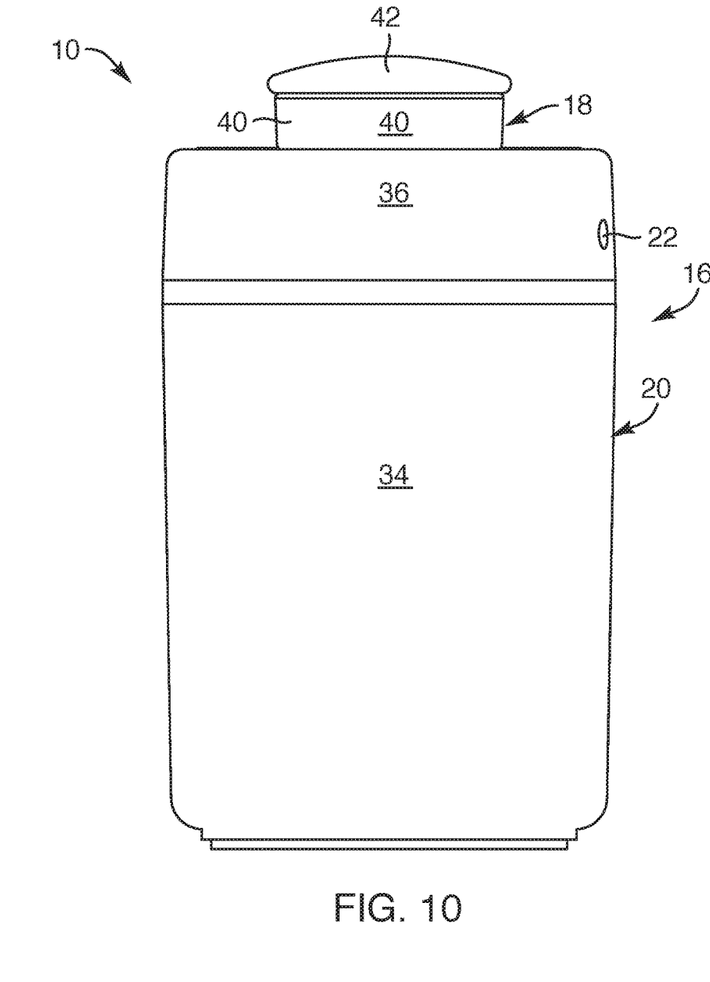
FIG. 10 is a rear elevation view thereof.
Figure 11:
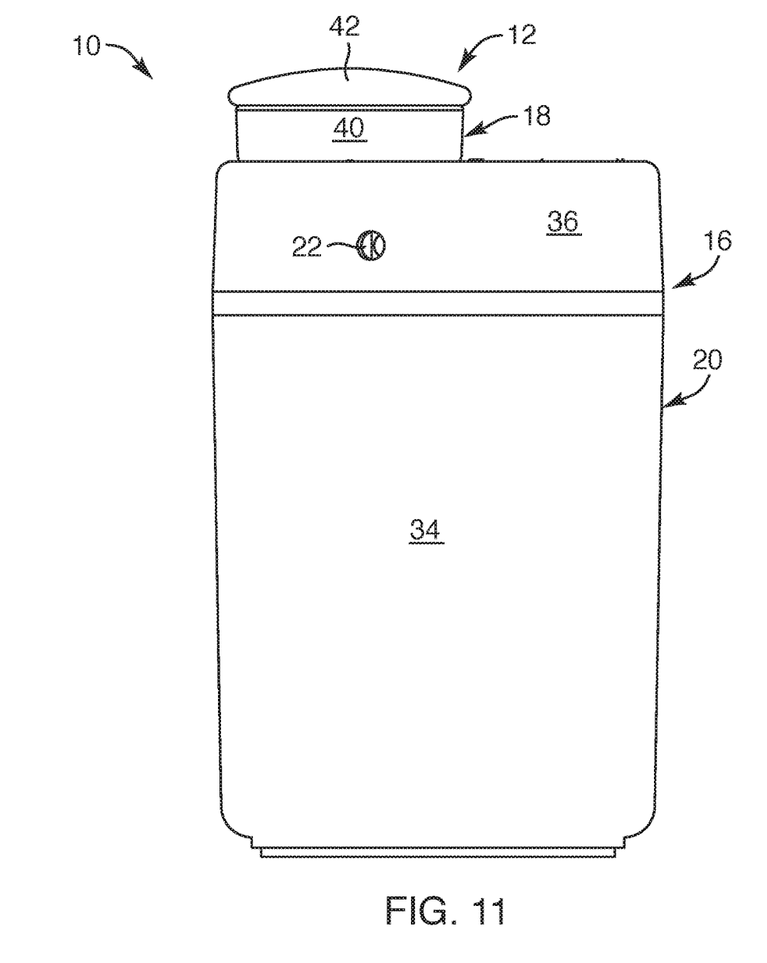
FIG. 11 is a left side elevation view thereof.
Figure 12:
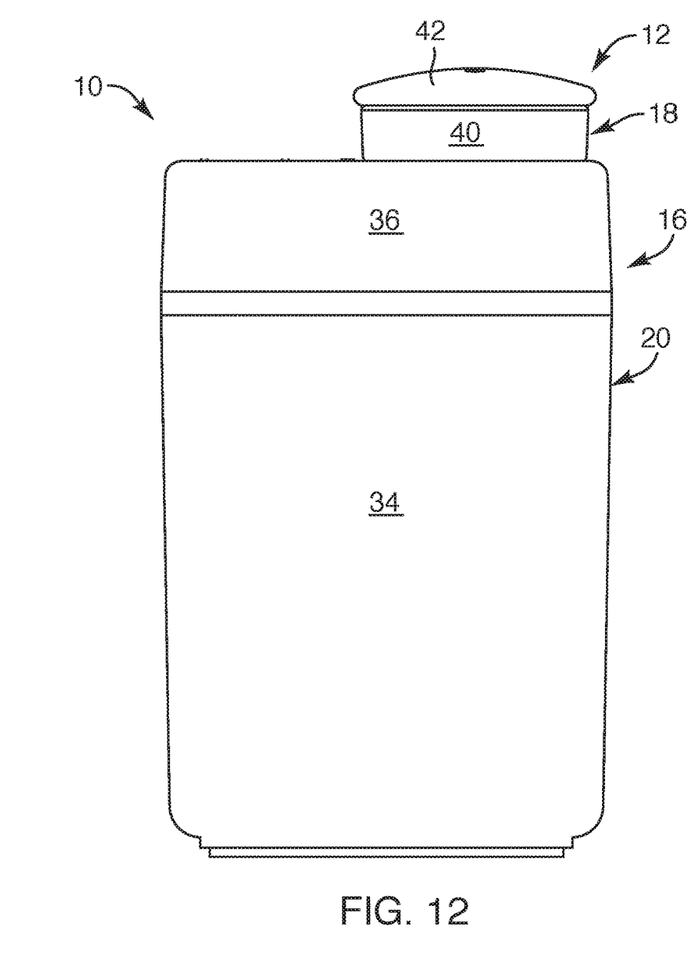
FIG. 12 is a right side elevation view thereof.

Referring to FIGS. 10 through 12, one can see that the housing 18 of the diffuser 12 is offset from center. In the front elevation view of FIG. 9 and the rear elevation of FIG. 10, the system 10 appears substantially symmetric, except for the power port 22 on the back half of the cap 36. In contrast, the left and right views, respectively, of FIGS. 11 and 12 illustrate the asymmetry of the diffuser 12 and its housing 18. Some embodiments may be permissible that would be completely symmetric in all the foregoing four views. However, with a compact pump assembly 100, the offset may be necessary in order to accommodate both the pump assembly 100 and the diffuser 12 in its housing 18, all within the housing 20 of the base 16.

Figure 13:
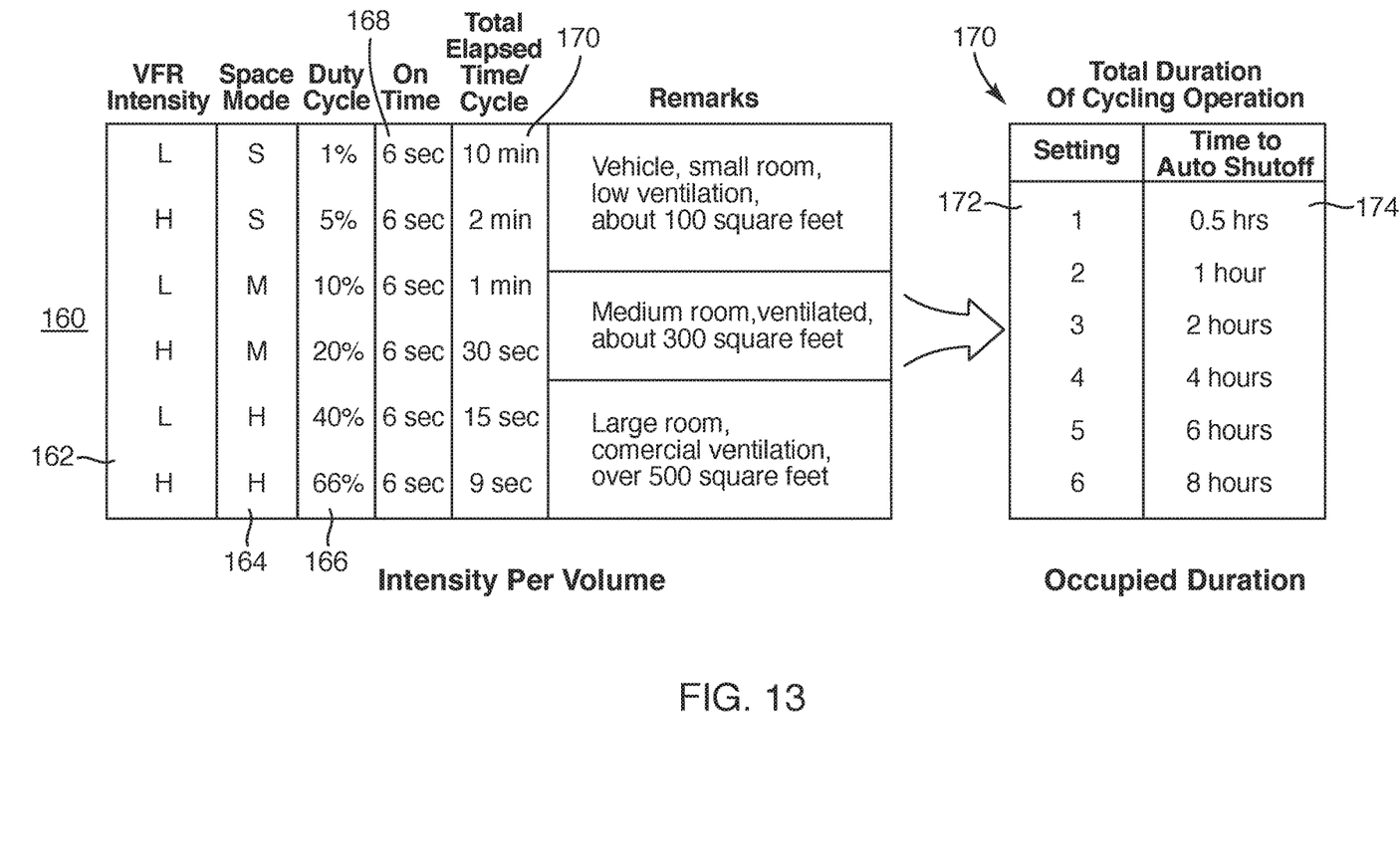
FIG. 13 is a schematic diagram and chart illustrating the control configuration for mapping operation and duty cycles of a system in accordance with the invention to a simplified scheme more easily understood and controlled by a user with limited numbers and buttons and decisions.

Referring to FIG. 13, several variables, mathematically speaking are controllable in order to provide a desired result. As a practical matter, however, a user would have to work through a rather complex process of either calculation and instruction, or alternatively, of trial and error. That is, determining what duty cycle the system 10 should operate on is partly a matter of taste, but also a matter of practicality. The amount of space or volume to be conditioned by a diffuser 12 will necessarily effect how much diffusion time of the total time the system 10 should operate. In the chart of FIG. 13 one can see a system of settings. The settings correspond to the buttons 24, 26, 28.

Referring to FIG. 13, while continuing to refer generally to FIGS. 1 through 13, a chart 160 illustrates settings for an intensity, or volumetric flow rate value 162, aligned beside various values of a space mode 164. The volumetric flow rate or intensity may be set at multiple levels. However, for purposes of illustration, here only a low (L) and a high (H) are shown. Likewise, for space mode, a volume or room size is identified by small (S), medium (M), and large (L) or high (H). One embodiment for a duty cycle 166 is illustrated.

Each of these duty cycles 166 or values of duty cycle 166 may correspond to any ratio of time in an "on" condition to total elapsed time desired. However, it has been found that the values of "on" time 168 to total elapsed time 170 are well served at the values illustrated. Accordingly, a duty cycle ranges from about one percent to about 66 percent of total elapsed time.

Finally, the duration portion 170 of the chart 160 identifies settings 172 and corresponding duration times 174. It has been found that a range of from about half an hour to about six hours will provide adequate options. Even in a work environment, where a user may remain for eight hours, a user may elect to only operate a system 10 for six hours, allowing a dissipation of the intensity of conditioned air over the last hours of the day.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An apparatus comprising: a housing; a drive system capable of drawing in and pressurizing a stream of air; a first sleeve enclosed completely within the housing and being sized, shaped, and positioned to enclose the drive system, thereby defining an annulus capable of passing the stream along an outer surface of the drive system; a reservoir capable of containing a liquid to be atomized by the stream; an atomizer capable of connecting in fluid communication with the reservoir, to receive a portion of the liquid therefrom, and in fluid communication with the drive system, to receive at least a portion of the stream therefrom, thereby spraying the stream of air carrying droplets formed from the portion of the liquid; a second sleeve enclosed completely within the housing and capable of enclosing the reservoir and atomizer, together selectively insertable into and removable from the second sleeve without tools; the drive system and atomizer capable of connecting in a fluid-sealing relation to feed the stream from the drive system into the atomizer when the atomizer is fitted into the second sleeve; wherein the annulus operates as a cooling channel cooling the drive system by passing the stream around the drive system upon entry into the apparatus.

2. The apparatus of claim 1, further comprising a housing cap enclosing the outer wall to form the housing.

3. The apparatus of claim 1, wherein the sleeve is provided a sleeve cap enclosing the reservoir, the atomizer, and the separator.

4. The apparatus of claim 1, further comprising:

a controller operably disposed in the housing cap and comprising buttons controlling a duty cycle of the drive system, wherein duty cycle represents a relationship between a duration of continual operation and at least one of total elapsed time and a duration of continual non-operation following the continual operation.

5. The apparatus of claim 1, further comprising:

at least one drift chamber operably connected in fluid communication, in series, with a separator to remove a portion of the second droplets from the stream.

6. The apparatus of claim 1 wherein a separator is provided in the apparatus that requires at least four changes in direction of the stream between the atomizer and an exit from the apparatus.

7. The apparatus of claim 1, wherein the atomizer is structured and located to discharge the stream vertically.

8. The apparatus of claim 7, wherein the atomizer is oriented to discharge the stream toward the liquid in the reservoir.

9. The apparatus of claim 1, further comprising a controller operably connected to the drive system to control the duty cycle of the drive system based on a size of space to be conditioned by the droplets and an intensity of conditioning of the space, both selected by a user and controlled by the drive system duty cycle, where duty cycle is represented by a relationship between a first time span in which the drive system operates and a second time span selected from total elapsed time and time spent by the drive system not operating.

10. An apparatus comprising:
a drive system providing a stream of air pressurized above an ambient;
walls, comprising an outer wall and an inner wall forming a space containing the drive system;
a housing defined by the outer wall;
a sleeve defined by the inner wall, shaped to hold a reservoir containing a liquid to be atomized, the sleeve being selectively removable from the housing;
an atomizer, within the sleeve and in fluid communication with the drive system when the sleeve is positioned in the housing, capable of fluid communication with the reservoir to draw the liquid along a liquid path therefrom due to momentum from the stream through the atomizer, and capable of atomizing and spraying the liquid as droplets in the stream along a vapor path;
a seal between the sleeve and the housing capable of connecting the drive system to feed the stream into the atomizer when the sleeve is fitted into the housing;
a separator connected to be capable of receiving the droplets from the atomizer and separating the droplets into first droplets sufficiently small to remain entrained in the stream while exiting from the apparatus and second droplets sufficiently large to be coalesced to liquid and thereby remain captured in the apparatus;
wherein a region between the drive system and the outer wall operates as a cooling channel cooling the drive system by passing the stream around the drive system upon entry into the apparatus.

11. The apparatus of claim 10, further comprising a housing cap enclosing the outer wall to form the housing.

12. The apparatus of claim 10, wherein the sleeve is provided a sleeve cap enclosing the reservoir, the atomizer, and the separator.

13. The apparatus of claim 10, further comprising:
a controller operably disposed in the housing cap and comprising buttons controlling a duty cycle of the drive system, wherein duty cycle represents a relationship between a duration of continual operation and at least one of total elapsed time and a duration of continual non-operation following the continual operation.

14. The apparatus of claim 10, further comprising:
at least one drift chamber operably connected in fluid communication, in series, with the separator and capable of moving a portion of the second droplets from the stream.

15. The apparatus of claim 10, wherein the atomizer is structured and located to discharge the stream vertically.

16. The apparatus of claim 10, wherein the atomizer is oriented to discharge the stream toward the liquid in the reservoir.

17. The apparatus of claim 10, further comprising a controller operably connected to the drive system to control the duty cycle of the drive system based on a size of space to be conditioned by the droplets and an intensity of conditioning of the space, both selected by a user and controlled by the drive system duty cycle, where duty cycle is represented by a relationship between a first time span in which the drive system operates and a second time span selected from total elapsed time and time spent by the drive system not operating.

* * * * *